US010479852B2

(12) United States Patent
Kim et al.

(10) Patent No.: US 10,479,852 B2
(45) Date of Patent: Nov. 19, 2019

(54) HYDROCHROMIC POLYDIACETYLENE COMPOSITE COMPOSITION, HYDROCHROMIC THIN FILM USING SAME, AND USE THEREOF

(71) Applicant: IUCF-HYU (INDUSTRY-UNIVERSITY COOPERATION FOUNDATION HANYANG UNIVERSITY), Seoul (KR)

(72) Inventors: Jong-Man Kim, Seoul (KR); Chan Woo Lee, Seoul (KR); Joosub Lee, Seoul (KR); Dong-Hoon Park, Gyeonggi-do (KR)

(73) Assignee: IUCF-HYU (INDUSTRY-UNIVERSITY COOPERATION FOUNDATION HANYANG UNIVERSITY) (KR)

( * ) Notice: Subject to any disclaimer, the term of this patent is extended or adjusted under 35 U.S.C. 154(b) by 208 days.

(21) Appl. No.: 15/468,072

(22) Filed: Mar. 23, 2017

(65) Prior Publication Data

US 2017/0190814 A1 Jul. 6, 2017

Related U.S. Application Data

(63) Continuation of application No. 14/761,132, filed as application No. PCT/KR2014/000522 on Jan. 17, 2014, now abandoned.

(30) Foreign Application Priority Data

Jan. 18, 2013 (KR) .................. 10-2013-0005923
Jan. 16, 2014 (KR) .................. 10-2014-0005403

(51) Int. Cl.
*C08F 138/02* (2006.01)
*C09D 149/00* (2006.01)
(Continued)

(52) U.S. Cl.
CPC .......... *C08F 138/02* (2013.01); *A61B 5/1172* (2013.01); *A61B 5/4266* (2013.01);
(Continued)

(58) Field of Classification Search
CPC ........ C08F 38/00; C08F 38/02; A61B 5/1172; G01N 31/22; G01N 31/222
See application file for complete search history.

(56) References Cited

U.S. PATENT DOCUMENTS 4,373,032 A * 2/1983 Preziosi .................. B01J 39/20
521/38
4,562,141 A * 12/1985 Tieke ...................... G03F 7/025
252/600

(Continued)

FOREIGN PATENT DOCUMENTS

JP 58143257 A * 8/1983 ........... G01N 27/121
JP 61036611 A * 2/1986 ............... F23G 5/50
(Continued)

OTHER PUBLICATIONS

Fund (Chapter 3: Transportation Labels and Placards:Technology, Handbook of Chemical Industry Labeling, 1984, Park Ridge, NJ, pp. 63-86).*

(Continued)

*Primary Examiner* — Brieann R Johnston
(74) *Attorney, Agent, or Firm* — Mark E. Bandy; Rankin, Hill & Clark LLP

(57) ABSTRACT

The present invention relates to a hydrochromic polydiacetylene composite composition, a hydrochromic thin film using same, and a use thereof, and more specifically, to a hydrochromic polydiacetylene composite composition reacting sensitively to moisture, providing the hydrochromic thin film using same, and to applying same to biorecognition or fingerprint recognition. According to the present inven- (Continued)

tion, moisture secreted from a fingerprint or pores on the skin can be detected with high sensitivity. Thus, the position of pores unique to a fingerprint of an organism can be amplified and displayed through selective color change and fluorescent change patterns exhibited when moisture is absorbed.

9 Claims, 11 Drawing Sheets

(51) Int. Cl.
| | |
|---|---|
| C08F 38/00 | (2006.01) |
| C08F 38/02 | (2006.01) |
| A61B 5/1172 | (2016.01) |
| G01N 31/22 | (2006.01) |
| G01N 21/81 | (2006.01) |
| C08F 138/00 | (2006.01) |
| C08F 2/44 | (2006.01) |
| C08F 238/00 | (2006.01) |
| A61B 5/00 | (2006.01) |
| C08L 49/00 | (2006.01) |

(52) U.S. Cl.
CPC .............. *C08F 2/44* (2013.01); *C08F 38/00* (2013.01); *C08F 38/02* (2013.01); *C08F 138/00* (2013.01); *C08F 238/00* (2013.01); *C09D 149/00* (2013.01); *G01N 21/81* (2013.01); *G01N 31/22* (2013.01); *G01N 31/222* (2013.01); *C08L 49/00* (2013.01)

(56) References Cited

U.S. PATENT DOCUMENTS

| | | | |
|---|---|---|---|
| 4,788,151 A * | 11/1988 | Preziosi | C07C 275/20 |
| | | | 116/206 |
| 5,731,112 A | 3/1998 | Lewis et al. | |
| 7,719,422 B1 | 5/2010 | Steinmetz et al. | |
| 10,150,133 B2 * | 12/2018 | Johnson | B05B 12/26 |
| 2002/0034475 A1 * | 3/2002 | Ribi | C07C 233/20 |
| | | | 424/9.6 |
| 2003/0143188 A1 | 7/2003 | Ribi | |
| 2004/0211939 A1 | 10/2004 | Elliott | |
| 2005/0171317 A1 | 8/2005 | Keller et al. | |
| 2011/0059867 A1 | 3/2011 | Kim et al. | |
| 2011/0091391 A1 | 4/2011 | Ribi | |
| 2016/0349223 A1 * | 12/2016 | Kim | G01N 31/222 |

FOREIGN PATENT DOCUMENTS

| | | |
|---|---|---|
| KR | 10-0815515 | 3/2008 |
| KR | 10-1007535 | 7/2010 |
| KR | 10-1079789 | 11/2010 |
| KR | 10-2012-0113947 | 10/2012 |
| KR | 10-2011-0199417 | 11/2012 |
| KR | 10-2015-0083814 | 7/2015 |

OTHER PUBLICATIONS

Miller (Copolymerization of Diacetylenes in the Crystalline Solid State. A Method for Recording Latent Fingerprints. Journal of Applied Polymer Science, vol. 24, 1979, pp. 883-886).*
Derwent Abstract of JP 01-36611 (Derwent Acc. No. 1989-082535, 1989, 3 pages).*
JPO Abstract of JP 58-143257 (1983, 2 pages).*
Agh-Atabay (Synthesis and Characterisation of Carboxylic Acid and Diphenylphosphine Derivatives in the 1,3-Diyne Series: Spectral Properties of Polydiacetylene Carboxylates. Polymer International, 31, 1993, pp. 367-374).*
DeGrazia (Diacetylene copolymers for fingermark development. Forensic Science International, 216, 2012, pp. 189-197).*
Bora Yoon et al., Practical Applications of Conjugated Polydiacetylene-Based Sensors, Polymer Science and Technology 2012, vol. 23, No. 6, p. 608-614.
Yevgeniy Lifshitz et al., Structural transitions in polydiacetylene langmuir films, Langmuir, 2009, vol. 25, No. 8, p. 4469-4477.
Xiaoqiang Chen et al., Biosensors and chemosensors based on the optical responses of polydiacetylenes, Chemical Society Reviews, 2012, vol. 41, No. 13, p. 4610-4630.
Thichamporn Eaidkong et al., Polydiacetylene paper-based colorimetric sensor array for vapor phase detection and identification of volatile organic compounds, Journal of Materials Chemistry, 2012, vol. 22, No. 13, p. 5970-5977.
Zhanfang Ma et al., Fabrication of stable polydiacetylene vesicles with 2,4-akyl-diacetylenic acid, Colloids and Surfaces A: Physicochemical and Engineering Aspects, 2007, vol. 303, No. 3, p. 179-183.
Jung Lee et al., Detection of adulterated gasoline using colorimetric organic microfibers, Journal of Materials Chemistry, 2011, vol. 21, p. 2648-2655.
International Search Report and Written Opinion; PCT/KR2014/000522; dated May 13, 2014; 9 pages.
European Search Report; dated Jun. 9, 2016; App.No. PCT/KR2014000522 (7 Pages).
PCT International Preliminary Report on Patentability; dated Jul. 30, 2015; App.No. PCT/KR2014000522 (15 Pages).

* cited by examiner

HYDROCHROMIC POLYDIACETYLENE COMPOSITE COMPOSITION, HYDROCHROMIC THIN FILM USING SAME, AND USE THEREOF

CROSS REFERENCES TO RELATED APPLICATIONS

This application is a continuation application of co-pending application Ser. No. 14/761,132 filed Jul. 15, 2015, which is a US national stage application under § 371 of international application No. PCT/KR2014/000522 filed Jan. 17, 2014.

TECHNICAL FIELD

The present invention relates to a hydrochromic polydiacetylene composite composition, a hydrochromic thin film using the same, and use thereof. More particularly, the present invention relates to a hydrochromic polydiacetylene composite composition that is highly sensitive to water, a hydrochromic thin film using the same, and the use thereof in biometrics or fingerprint recognition.

BACKGROUND ART

Polydiacetylenes are polymers of diacetylene monomers, with a backbone structure characterized by the alternate carbon double bond and carbon triple bond therein. When being close enough to each other to form a crystalline or semi-crystalline state, diacetylene monomers undergo polymerization under UV or gamma radiation to afford the conjugated polymers. An aqueous dispersion of polydiacetylene in a suitable condition or a thin film of polydiacetylene on a solid substrate appears blue with a maximum absorbance peak at about 650 nm. Upon exposure to external stimuli (e.g., heat, solvents, pH, molecular recognition, etc.), polydiacetylenes can change in color from blue to red with a maximum absorbance peak at about 550 nm. This characteristic of color transition under specific conditions has recently inspired active research into the use of polydiacetylene as various sensors. As far as polydiacetylene-based sensors are concerned, reference may be made to Korean Patent No. 10-1199417, and Journal of Materials Chemistry, 21, 2648-2655 (2011), which both pertain to polydiacetylene-based polymer sensor fibers, and use thereof in detecting adulterated gasoline. Nowhere has the application of polyacetyelene to fingerprint recognition been mentioned in previous documents.

A fingerprint is an impression left by the friction ridges of a human finger. Fingerprints, the recovery of which from a crime scene is an important method of forensic science, are easily deposited on suitable surfaces by the natural secretions of sweat from the eccrine glands, epocrine glands, and sebaceous glands that are present in epidermal ridges. The secretions are composed mostly of water, together with a minor portion of inorganic materials such as chlorides and metal ions, and organic materials such as amino acids, urea, proteins, carbohydrates, and fatty acids. These secretions are colorless and thus invisible to the naked eye. In the present invention, polydiacetylenes are remarkably improved in chromatic transition and fluorescent change by modifying the diacetylene moieties with alkali metal ionic compounds, thereby being able to highly sense even a trace of water secreted from sweat pores in the friction ridges. When fingers are pressed against the thin film of the present invention, not only do friction ridge patterns appear thereon, but also a distribution of sweat pores in the ridges is distinctively shown, thus visualizing a distribution map of sweat pores. Each person has their own peculiar friction ridge patterns, and is also different from one to another in the distribution of sweat pores in the friction ridges. Thus, even a very small portion of the sweat pore map printed on the thin film can guarantee the intrinsic fingerprint characteristics of the fingerprint provider of interest. As mentioned above, a combination of the fingerprint and the distribution map of sweat pores, obtained according to the present invention can approximate the fingerprint recognition rate to 100%, and can be used to prevent the crime of fingerprint forgery. The present invention is an original technology because it has not been reported thus far.

[Related Art Document] Korean Patent No. 10-1199417.

DISCLOSURE

Technical Problem

The present disclosure is to provide a hydrochromic polydiacetylene composite composition sensitively reactive to water, a hydrochromic thin film using the same, and the use thereof in biometrics or fingerprint recognition. Also, provided are respective methods for producing a hydrochromic polydiacetylene composite composition, and for fabricating a hydrochromic thin film.

Technical Solution

In accordance with an aspect thereof, the present invention addresses a method for producing a hydrochromic polydiacetylene composite composition, comprising: dissolving an alkali metal ionic compound in water to give a first solution (step a); dissolving a diacetylene monomer in an organic solvent to give a second solution (step b); and stepwise adding a small amount of the first solution to the second solution, and mixing the first solution and the second solution together by stirring to give a diacetylene composite, followed by photopolymerization (step c). The alkali metal may include at least one metal selected from the group consisting of cesium, rubidium, potassium, sodium, and lithium.

As used herein, the term "diacetylene composite" refers to a compound in which a diacetylene monomer is conjugated with an alkali metal ionic compound.

The photopolymerization of step c may be the polymerization of a self-assembled diacetylene composite under light.

The self-assembly may be achieved by changing the solution in solubility, or applying the solution as a film onto a substrate such as glass, a PET film, an OHP film, etc.

Adapted to interact with an alkali metal ionic compound to afford a composite, the diacetylene monomer may be a diacetylene molecule containing both a functional group, such as carboxylic acid, and a hydrophobic alkyl chain, as represented by the following Chemical Formula 1:

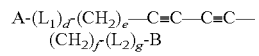 [Chemical Formula 1]

wherein d+g is an integer of 0, 1 or 2, e+f is an integer of 2 to 50 wherein e and f are independently integers of 1 or greater; A and B independently represent methyl, amine, carboxyl, hydroxy, maleimide, biotin, N-hydroxysuccinimide, benzoic acid, or activated ester, and may be in an ionized state; and $L_1$ and $L_2$, which may be the same or different, independently represent alkyl of 2 or more carbon atoms, one or more ethylene oxides, amine, amide, ester, or carbonyl.

The diacetylene monomer may be a compound represented by the following Chemical Formula 2, or an mBzA compound in which a benzamide group is incorporated into a diacetylene molecule. These compounds are representative monomer moieties that can induce irreversible and reversible chromatic transition, respectively.

[Chemical Formula 2]

wherein m+n is an integer of 2 to 50.

A polydiacetylene undergoes an irreversible chromatic transition from a blue to a red phase if consisting of pure diacetylene monomers, but the transition may be reversible if consisting of mBzA compound because the benzamide group provides resilience for the polydiacetylene molecules. That is, the mBzA compound responds to an external stress, and recovers the original state due to the intermolecular hydrogen bonds of the amide groups after removal of the external stresses. Thus, the employment of the mBzA compound is advantageous in that the polymer can be repetitively used in fingerprint authentication as will be described below.

The diacetylene monomer may be selected from the group consisting of PCDA (10,12-pentacosadiynoic acid), TCDA (10,12-tricosadiynoic acid), HCDA (8, 10-heneicosadiynoic acid), PCDA-mBzA, TCDA-mBzA, HCDA-mBzA, and a combination thereof.

Structures of PCDA, TCDA, and HCDA are given in Structural Formula 1.

TABLE 1

Comparison of Atomic Diameters

| | Atomic Diameter | Van der Waals diameter |
|---|---|---|
| Li Ion | 0.304 nm | 0.364 nm |
| Na Ion | 0.372 nm | 0.454 nm |
| K Ion | 0.454 nm | 0.496 nm |
| Rb Ion | 0.496 nm | 0.606 nm |
| Cs Ion | 0.530 nm | 0.686 nm |

DddAn alkali metal ionic compound with a larger metal ion radius reacts with a carboxylic acid of the diacetylene monomer moiety to form a larger ionic salt, which leads to greater repulsion to adjacent ionic salts. When absorbing water molecules, the ionic salts exhibit great repulsion to distort the molecular structure, resulting in chromatic or fluorescent transition. Since cesium has the largest ion radius of the alkali metals, the composite composition based on the diacetylene monomers coupled with cesium hydroxide most sensitively responds to water absorption. For the condition that needs less sensitivity to water, smaller alkali ions may be employed. Considering the ion radius thereof, the amount of alkali metal ions is determined depending on the use of the diacetylene composite composition.

Based on a mole of the diacetylene monomer, the alkali metal ionic compound may be used in an amount of 0.1 to 3 moles and preferably in an amount of 0.5 to 2 moles. Given the alkali metal ionic compound within the range, the composite composition can suitably respond to water, and has improved stability. When the alkali metal ionic compound is used in an amount less than 0.1 mole, the compo-

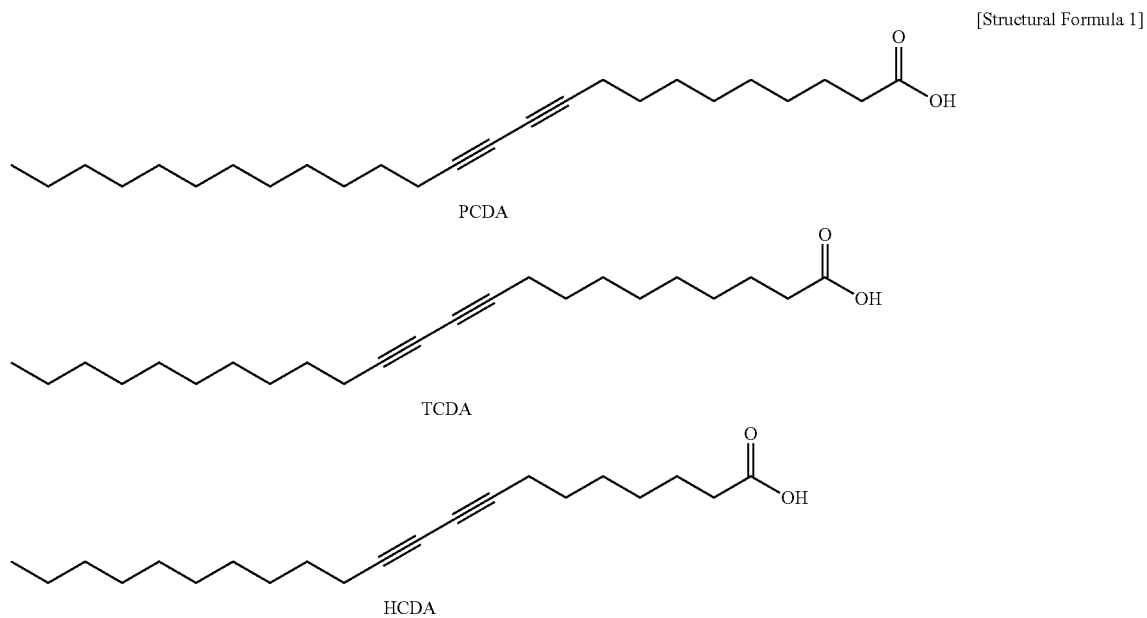

[Structural Formula 1]

For use in the preparation of the diacetylene composite, the alkali metal ionic compound responds with water and shows hygroscopicity. The alkali metal ionic compound used in the present invention may include at least one selected from the group consisting of lithium hydroxide, sodium hydroxide, potassium hydroxide, rubidium hydroxide, and cesium hydroxide, and preferably from among rubidium hydroxide and cesium hydroxide.

sition may decrease in sensitivity to water. On the other hand, more than 3 moles of the alkali metal ionic compound to a mole of diacetylene monomer may increase the degree of ionization of the composition to the extent of crystallization.

As described above, the alkali metal ions undergo an acid-base reaction with the carboxylic acid of the diacetylene monomer moiety to form an ionic salt composite.

The diacetylene composite may be or may comprise at least one of the compounds represented by the following Chemical Formulas 3 to 7.

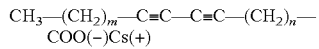  [Chemical Formula 3]

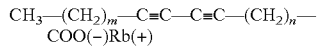  [Chemical Formula 4]

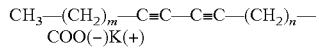  [Chemical Formula 5]

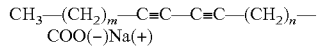  [Chemical Formula 6]

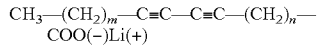  [Chemical Formula 7]

wherein m+n is an integer of 2 to 50.

The polydiacetylene composite composition may be obtained by exposing the diacetylene monomers to UV or gamma radiation when they are close enough to each other to form a crystalline or semi-crystalline state.

The organic solvent may include at least one selected from the group consisting of alcohol, acetone, dioxane, THF (tetrahydrofuran), and DMF (dimethylformamide).

In accordance with another aspect thereof, the present invention addresses a method for fabricating a hydrochromic thin film, comprising: dissolving an alkali metal ionic compound in water to give a first solution; dissolving a diacetylene monomer in an organic solvent to give a second solution; stepwise adding a small amount of the first solution to the second solution, and mixing the first solution and the second solution together by stirring to give a diacetylene composite; and coating a substrate with the diacetylene composite and photopolymerizing the diacetylene composite on the substrate.

Descriptions on the alkali metal ionic compound, the diacetylene monomer, and the organic solvent are omitted because they are as defined above.

The substrate may be selected from the group consisting of glass, a PET film, and an OHP film. The coating may be obtained using a method selected from the group consisting of spin coating, inkjet printing, a doctor blade technique, and dip-drawing.

For spin coating, a powder of the diacetylene composite is added in an amount of 5 to 20 weight % to a pure organic solvent, and ultrasonicated to give a solution. To this solution, water is added in an amount of 1 to 30 volume % based on the total volume of the solution, followed by ultrasonication to prepare a spin coating solution.

For use in inkjet printing, the diacetylene composite is added to an aqueous solution containing a water-soluble organic solvent in an amount of 1 to 70 volume % based on the total volume of the aqueous solution, heated at around 70° C., and ultrasonicated.

Exposure to UV radiation causes the diacetylene composite on the substrate to polymerize into a shrunk polydiacetylene composite (see FIGS. 1 and 2). When arranged in such close contact with each other to form a crystalline or semi-crystalline structure, the diacetylene monomers can be polymerized into a polydiacetylene under UV and gamma radiation.

As described above, because the diacetylene composite contains ionic salts with large radii, there is repulsion between adjacent ionic salts. Because water absorbed to polymer further enlarges the repulsion, the polymer sensitively responds to water. In the presence of water, metal ions complexed with the monomer moieties further repulse adjacent ions and thus distort the molecular structure of the polymer, resulting in a change in color and fluorescence.

The polydiacetylene composite has an amphipathic molecular structure in which the monomers, each having a hydrophilic head and a hydrophobic tail, are arranged by self-assembly, as shown in FIG. 2. When the polydiacetylene composite is brought into direct or indirect contact with a water-containing secretion in a temperature environment similar to human body temperature, the hydrophilic head selectively absorbs water. In this regard, the heads swelling due to the absorbed water undergo relatively large spatial repulsion to distort the conjugated structure of the photopolymerized polydiacetylene, resulting in hydrochromic transition from a blue to a red phase (FIG. 4). In the conjugated structure of the photopolymerized polydiacetylene, the interchain length is 0.384 nm while alkali metals such as lithium, sodium, and potassium have an atomic diameter of approximately 0.4 nm or less. In the presence of a small amount of water, a polydiacetylene composite with a small alkali metal such as lithium or sodium may not show an instant color change because there is small interchain strain. In contrast, a polydiacetylene composite with a large alkali metal such as cesium, rubidium, or potassium retains large interchain strain due to the large metal atom diameter (cesium 0.530 nm, rubidium 0.496 nm, potassium 0.454 nm). Water absorbed into the hydrophilic head gives additional strain to the polymer to cause the functional group of the polydiacetylene to undergo orbital distortion, with the instant response of hydrochromism. Particularly cesium cations, which have the greatest atomic diameter among the alkali metals, receive the greatest strain from water, and thus respond to even a trace amount of water at a fast rate, resulting in hydrochromic transition. Moreover, the polydiacetylene composite can be reversibly or irreversibly changed in sensitivity to water and pH-dependent color transition by regulating a molar ratio between the diacetylene monomer and the alkali metal ionic compound. Hence, hydrochromic thin films suitable for surrounding conditions can be fabricated. That is, the concentration of the alkali metal such as cesium is adjusted so as for the polydiacetylene composite to respond to a predetermined amount of water. For instance, the cesium concentration may be adjusted such that the polyacetylene composite undergoes hydrochromic transition at a humidity of 5% or higher, or at a humidity of 50% or higher, or at a humidity of 100%. Therefore, the hydrochromic thin film according to the present invention may be used as a humidity sensor that sensitively responds to water.

After the photopolymerization, a blue insoluble hydrochromic thin film can be obtained. When absorbing water, the blue thin film turns red, emitting red fluorescence. This property allows the hydrochromic thin film to be used in fingerprint recognition. The present invention is characterized by the ability to clearly visualize fingerprints impressed faintly, and even visualize a part of sweat pore distribution into amplified fluorescent patterns, which is quite different from conventional methods of fingerprint recognition. Further, even a fluorescent pattern image of the sweat pore distribution partially impressed on the hydrochromic thin film can be used to discriminate forged and genuine fingerprints with an accuracy of near 100%. Hence, the present invention may be a technology for pioneering developments in the field of forensic science or fingerprint authentication.

In accordance with a further aspect thereof, the present invention addresses a hydrochromic polydiacetylene composite composition comprising a polydiacetylene polymerized from diacetylene monomers that are complexed with alkali metal ions.

The alkali metal may be selected from the group consisting of cesium, rubidium, potassium, sodium, lithium, and a combination thereof. Herein, for use in the preparation of the diacetylene composite, the alkali metal ionic compound responds with water and shows hygroscopicity. An alkali metal ionic compound with a larger metal ion radius responds with a carboxylic acid of the diacetylene monomer moiety to form a larger ionic salt, which leads to greater repulsion to adjacent ionic salts, allowing the diacetylene composite to respond sensitively to water. When cesium ions with large ion radius used, the composite sensitively respond to water. However, for the condition that needs less sensitivity to water, smaller alkali ions may be employed. Considering the ion radius thereof, the amount of alkali metal ions is determined depending on the use of the diacetylene composite composition.

Containing both a functional group, such as carboxylic acid, and a hydrophobic alkyl chain, the diacetylene monomer is adapted to interact with an alkali metal ionic compound to afford a composite. The diacetylene monomer may be a compound represented by either Chemical Formula 1 or 2, or may be an mBzA compound in which a benzamide group is incorporated into a diacetylene molecule, or may contain both of the compound of Chemical Formula 1 or 2, and the mBzA compound. Alternatively, the diacetylene monomer may be selected from the group consisting of PCDA (10,12-pentacosadiynoic acid), TCDA (10,12-tricosadiynoic acid), HCDA (8, 10-heneicosadiynoic acid), PCDA-mBzA, TCDA-mBzA, HCDA-mBzA, in which a benzamide group is incorporated into the diacetylene molecule, and a combination thereof. The diacetylene composite may be or may comprise any one of the compounds of Chemical Formulas 3 to 7.

In regard to the hydrochromic polydiacetylene composite composition according to the further aspect of the present invention, detailed descriptions of the alkali metal ionic compound, the diacetylene monomer, and the diacetylene composite are omitted because they are as defined above.

In accordance with a further aspect thereof, the present invention addresses a hydrochromic thin film, comprising a thin film substrate; and a coating layer, formed on the thin film substrate, including a hydrochromic polydiacetylene composite composition, the hydrochromic polydiacetylene composite composition comprising a polydiacetylene polymerized from diacetylene monomers that are complexed with alkali metal ionic compounds. The alkali metal may include at least one selected from the group consisting of cesium, rubidium, potassium, sodium, and lithium. The substrate may be selected from the group consisting of glass, a PET film, and an OHP film. Descriptions on the alkali metal ionic compound, the diacetylene monomer, the diacetylene composite, and the hydrochromic polydiacetylene composite composition are omitted because they are as defined above.

Sensitively undergoing color or fluorescent transition in instant response to water, as mentioned above, the hydrochromic thin film according to one embodiment of the present invention can be applied to biometrics or sweat gland mapping, as well as fingerprint recognition.

Herein, the term "sweat gland mapping", as used herein, refers to the manifestation of sweat pores in the form of a map. A sweat pore map can be readily obtained by lightly pressing a finger against the hydrochromic thin film after sebaceous secretions and oils on the finger are cleaned off. When a finger or hand is in contact with the hydrochromic thin film, a trace amount of sweat is secreted from sweat pores and causes the hydrochromic thin film to change in color selectively along the sweat pores. A sweat pore map can be manifested wherever sweat pores are present, for example, on the sole of a foot, the face, the arms, and the hands.

People are also different from each another in terms of the distribution of sweat pores in the friction ridges. Thus, because even a very small portion of the sweat pore map printed on the thin film can guarantee the intrinsic fingerprint characteristics of the fingerprint provider of interest, the hydrochromic thin film of the present invention can be applied to edge-cutting forensic science and fingerprint authentication.

In accordance with still another aspect thereof, the present invention addresses a humidity sensor for biometrics, based on a hydrochromic polydiacetylene composite composition comprising a polyacetlyene composite prepared by polymerizing a diacetylene composite formed by complexing a diacetylene monomer with an alkali metal ionic compound. The alkali metal of the alkali metal ionic compound may include at least one selected from cesium, rubidium, potassium, sodium, and lithium. The humidity sensor for biometrics may be used as a humidity sensor for fingerprint recognition. In accordance with yet another aspect thereof, the present invention addresses a method for measuring humidity, using the humidity sensor for biometrics. In this regard, humidity can be measured by taking advantage of the increasing degree of chromic transition with an increase in humidity.

Advantageous Effects

As described hitherto, the hydrochromic polydiacetylene composite composition of the present invention can undergo chromatic transition and fluorescent change when being in contact with water. Thanks to its high sensitivity to water, the hydrochromic polydiacetylene composite composition of the present invention can sense even a trace amount of water on the friction ridges of fingers or from sweat pores distributed along the friction ridges. Hence, the hydrochromic polydiacetylene composite composition of the present invention can exhibit intrinsic fingerprints and sweat pore locations on fingerprints positions in an amplified manner of color and fluorescent transition patterns.

Capable of recognizing the friction ridges and even a segment of sweat pores distributed along the friction ridges, the polydiacetylene composite composition of the present invention can be used to discriminate fingerprints, even if they remain highly partial, through comparison of characteristic sweat pore distribution patterns, and thus can perform fingerprint recognition with exceptionally improved accuracy.

In addition, the hydrochromic thin film based on the polydiacetylene composite composition in accordance with the present invention can visualize fingerprints impressed faintly and even a part of sweat pore distribution into amplified fluorescent patterns, and finds applications in various fields including forensic science, biometrics, forgery prevention, humidity sensors, etc. Particularly, the hydrochromic thin film is applied to a humidity sensor for biometrics thanks to its ability to sense even a trace amount of water.

Further, the present invention can be applied for a broad spectrum of commercial uses because water leakage from various facilities and constructions including water pipes, cracked structures, experimental instruments, etc. can be detected in situ by taking advantage of the color or fluorescent transition in response to water absorption.

MODE FOR INVENTION

Figure 1:
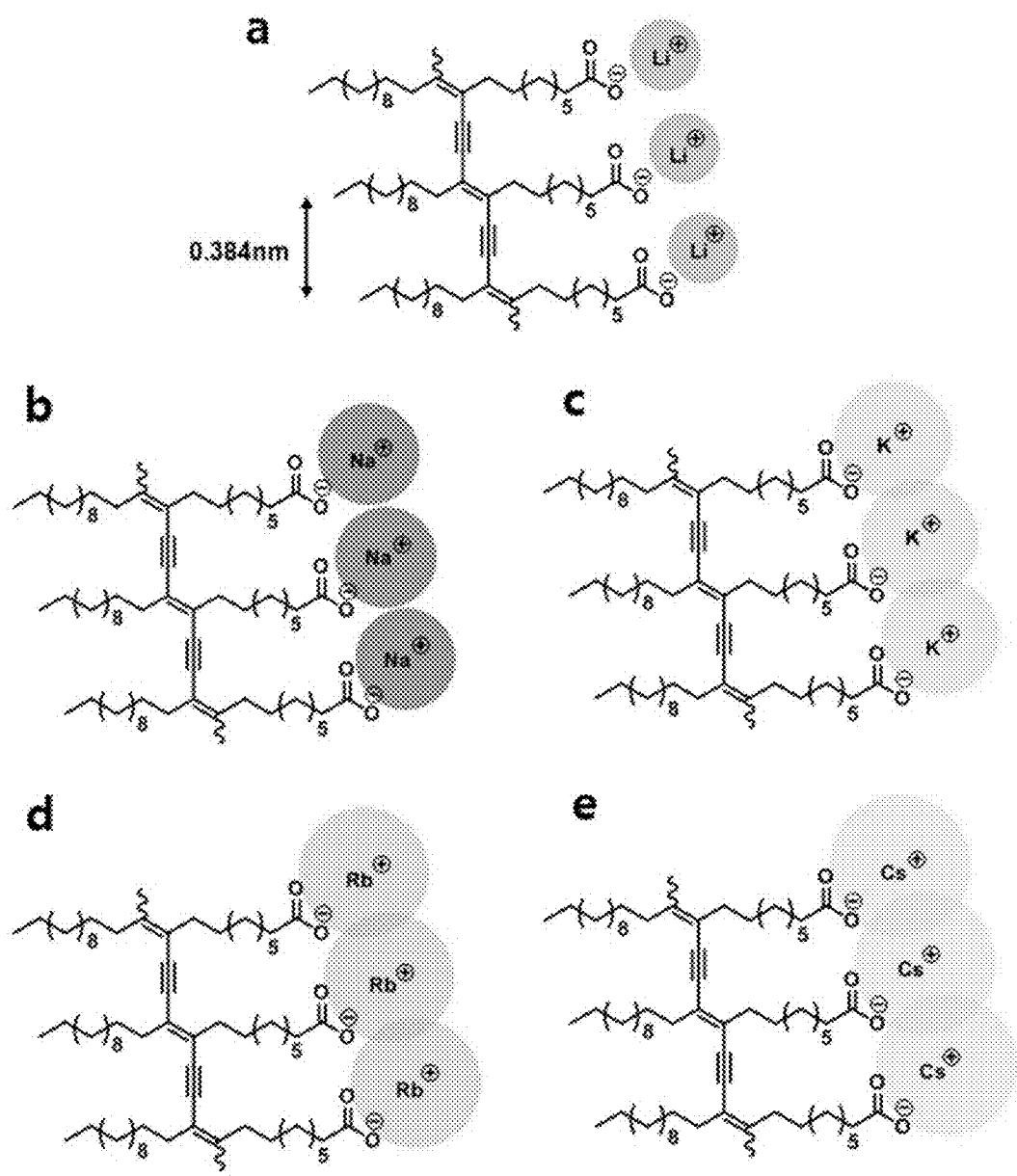
FIG. 1 shows schematic views of polydiacetylene structures photopolymerized from diacetylene monomers complexed with lithium (a), sodium (b), potassium (c), rubidium (d), and cesium (e) in accordance with exemplary embodiment of the present invention.
Figure 2:
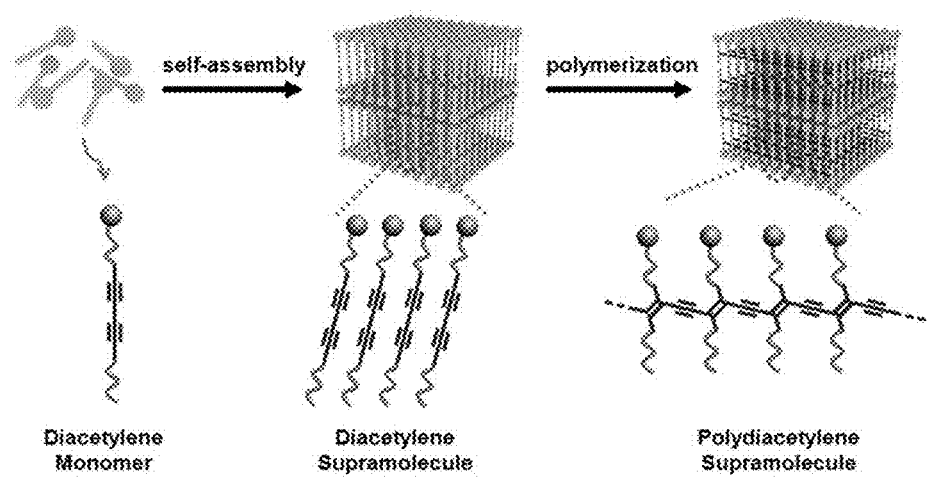
FIG. 2 is a schematic view illustrating a procedure of photopolymerizing diacetylene composites in accordance with an exemplary embodiment of the present invention.

A better understanding of the present invention may be obtained through the following examples that are set forth to illustrate, but are not to be construed as limiting the present invention.

Example 1: Preparation of Polydiacetylene Composite Composition

Example 1-1: Preparation of PCDA-Cs Polydiacetylene Composite Composition

A solution of 0.750 g of CsOH in deionized water was dropwise added to a solution of 1.87 g of PCDA (10,12-pentacosadiynoic acid) in 9.6 mL of THF (tetrahydrofuran), and mixed together by stirring for 1 hr. The mixed solution was left for self-assembly, and then subjected to photopolymerization under a 254 nm UV lamp to give a composite composition.

Example 1-2: Preparation of TCDA-Cs Polydiacetylene Composite Composition

A composite composition was prepared in the same manner as in Example 1-1 with the exception that TCDA (10, 12-tricosadiynoic acid) was used instead of PCDA.

Example 1-3: Preparation of PCDA-Rb Polydiacetylene Composite Composition

A composite composition was prepared in the same manner as in Example 1-1 with the exception that RbOH was used instead of CsOH.

Example 1-4: Preparation of HCDA-K Polydiacetylene Composite Composition

A composite composition was prepared in the same manner as in Example 1-1 with the exception that K and HCDA (8, 10-heneicosadiynoic acid) were used instead of CsOH and PCDA, respectively.

Example 1-5: Preparation of TCDA-K Polydiacetylene Composite Composition

A composite composition was prepared in the same manner as in Example 1-1 with the exception that K and TCDA (10, 12-tr icosadiynoic acid) were used instead of CsOH and PCDA, respectively.

Example 1-6: Preparation of TCDA-Rb Polydiacetylene Composite Composition

A composite composition was prepared in the same manner as in Example 1-1 with the exception that RbOH and TCDA were used instead of CsOH and PCDA, respectively.

Example 1-7: Preparation of HCDA-Na Polydiacetylene Composite Composition

A composite composition was prepared in the same manner as in Example 1-1 with the exception that Na and HCDA were used instead of CsOH and PCDA, respectively.

Example 2: Thin Film Fabrication 1

Example 2-1: Fabrication of PCDA-Cs Thin Film

A solution of 0.750 g of CsOH in deionized water was dropwise added to a solution of 1.87 g of PCDA (10,12- pentacosadiynoic acid) in 9.6 mL of THF (tetrahydrofuran), and mixed together by stirring for 1 hr. The resulting solution composition was applied onto a PET film using a spin coater at 2,000 rpm for 1 min to give a coating 0.5 μm thick. The coated thin film was dried at 70° C. for 1 min to give a photochromic or photopolymerizable supramolecule film, which was then exposed to 254 nm radiation from a UV lamp to afford a blue thin film.

Example 2-2: Fabrication of TCDA-Cs Thin Film

A blue thin film was fabricated in the same manner as in Example 2-1 with the exception that TCDA (10, 12-tricosadiynoic acid) was used instead of PCDA.

Example 2-3: Fabrication of PCDA-Rb Thin Film

A blue thin film was fabricated in the same manner as in Example 2-1 with the exception that RbOH was used instead of CsOH.

Example 2-4: Fabrication of HCDA-K Thin Film

A blue thin film was fabricated in the same manner as in Example 2-1 with the exception that K and HCDA (8, 10-heneicosadiynoic acid) were used instead of CsOH and PCDA, respectively.

Example 2-5: Fabrication of TCDA-K Thin Film

A blue thin film was fabricated in the same manner as in Example 2-1 with the exception that K and TCDA (10,12-tricosadiynoic acid) were used instead of CsOH and PCDA, respectively.

Example 2-6: Fabrication of TCDA-Rb Thin Film

A blue thin film was fabricated in the same manner as in Example 2-1 with the exception that RbOH and TCDA were used instead of CsOH and PCDA, respectively.

Example 2-7: Fabrication of HCDA-Na Thin Film

A blue thin film was fabricated in the same manner as in Example 2-1 with the exception that Na and HCDA were used instead of CsOH and PCDA, respectively.

Example 3: Thin Film Fabrication 2

A solution of 0.750 g of CsOH in deionized water was dropwise added to a solution of 1.87 g of PCDA (10,12-pentacosadiynoic acid) in 9.6 mL of THF (tetrahydrofuran), and mixed together by stirring for 1 hr. The resulting solution composition was 20-fold diluted in a solvent (dioxane/water 40% v/v), and then loaded to an inkjet cartridge mounted on an office inkjet printer. The dilution was printed on a PET film using the inkjet printer, and exposed to 245 nm radiation from a UV lamp to afford a thin film.

Test Example 1: Thin Film Characterization 1

Figure 3:
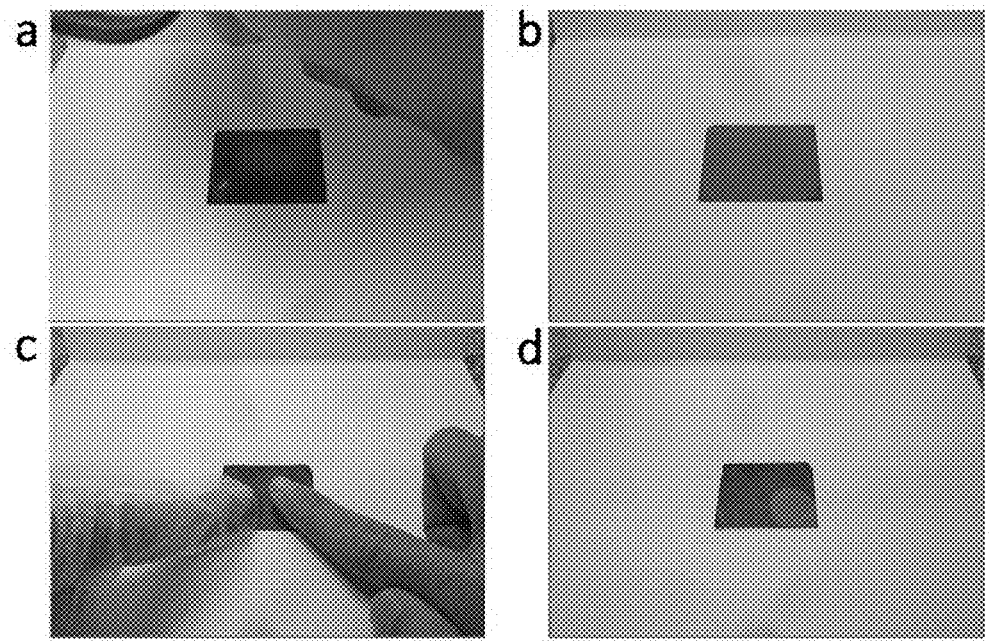
FIG. 3 illustrates the responsiveness to water of a hydrochromic thin film in accordance with an exemplary embodiment of the present invention.

As illustrated in FIG. 3, the blue thin film of Example 2-1 was carefully picked up with a forceps. The blue film turned red (b, d) within 1 sec after it was manually blown on by a researcher exhaling with a wide open mouth (near body temperature) (a) or after a finger was approached to the film at a distance of 0.3 mm (c). However, the blue film remained unchanged in color when the film was strongly blown on by a researcher exhaling from a narrow open mouth (lower than the body temperature due to adiabatic expansion), or when the film was sealed with a transparent wrap or tape before being breathed on or pressed by fingers.

Test Example 2: SEM Image and XRD Spectrum Analysis

Figure 4:
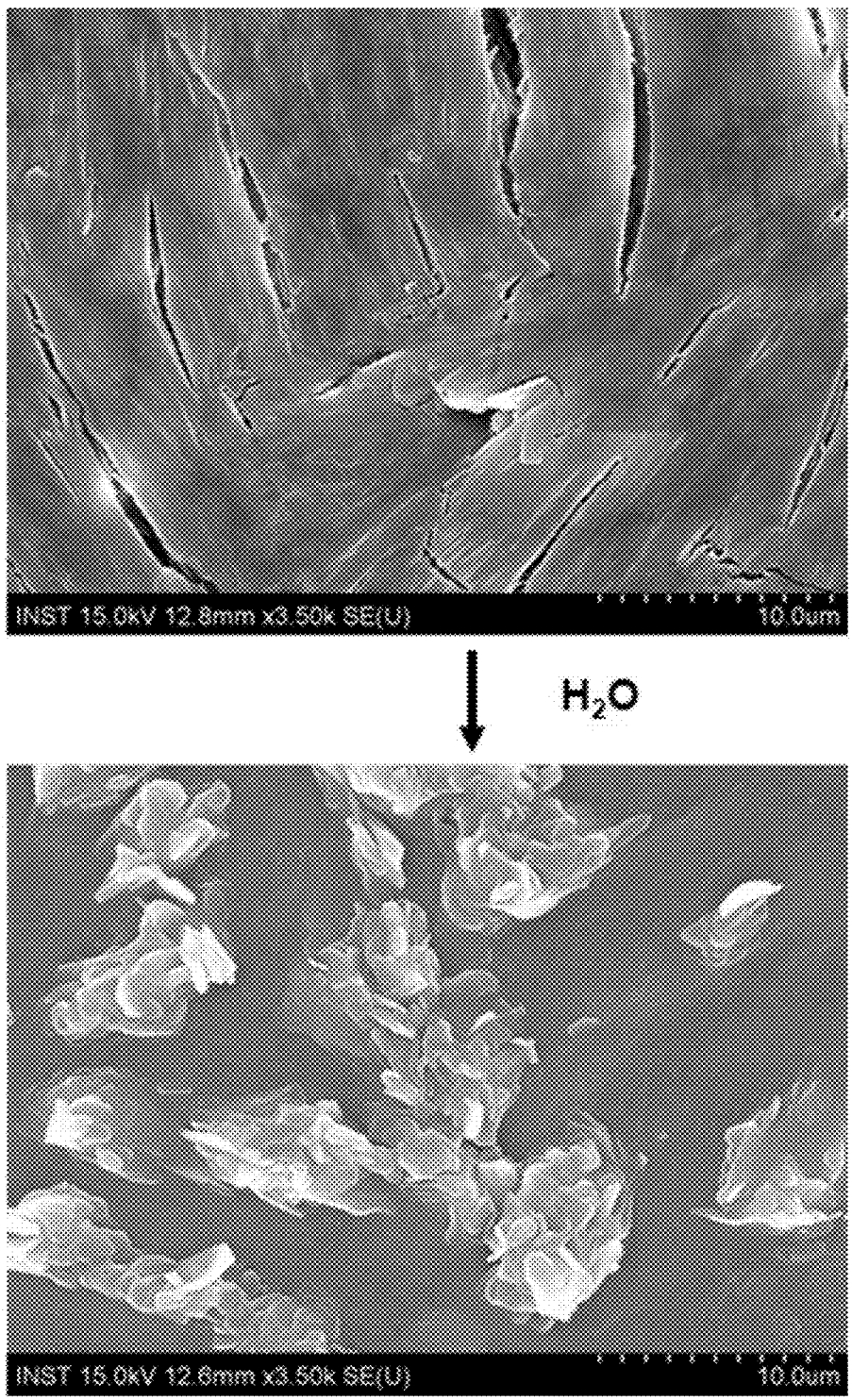
FIGS. 4 to 6 illustrate the structural change of a hydrochromic thin film in response to water absorption according to an exemplary embodiment of the present invention in SEM images (FIG. 4), XRD spectra (FIG. 5), and a schematic view (FIG. 6).
Figure 5:
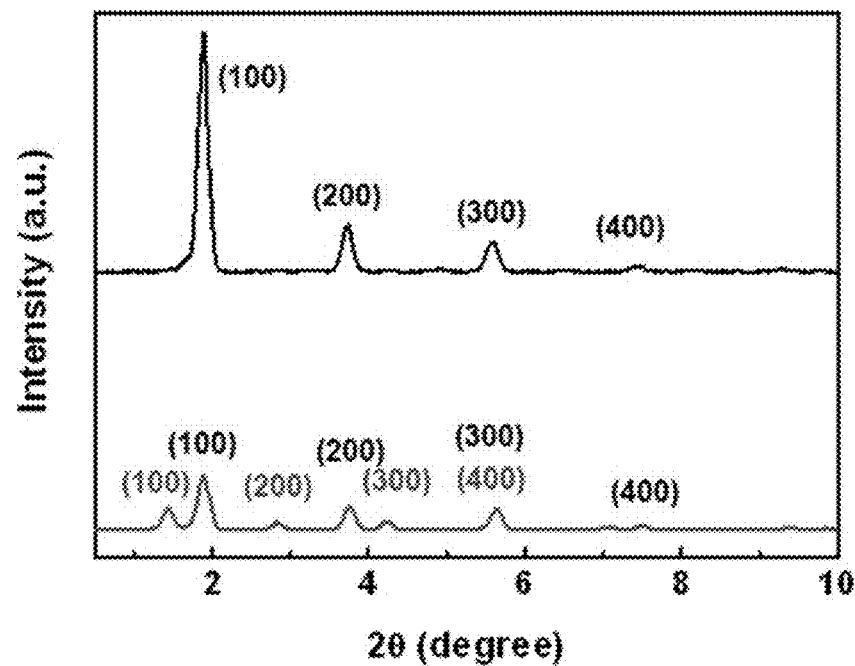
Figure 6:
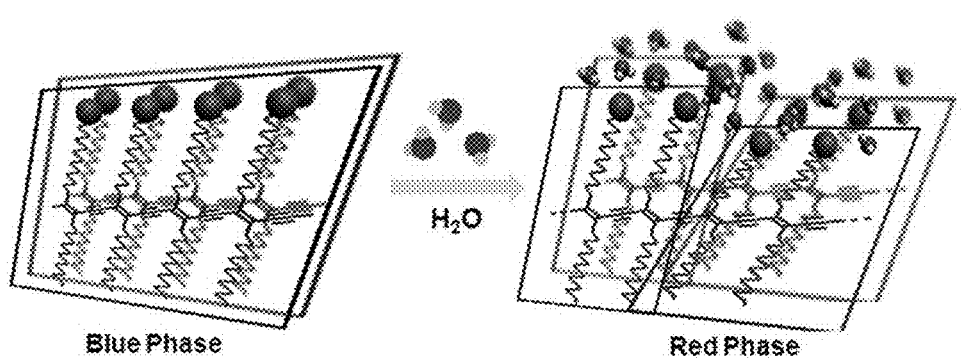

SEM images and XRD spectra of the thin film fabricated in Example 2-1 are given in FIGS. 4 and 5, respectively. FIG. 4 shows SEM images of the surface of the polydiacetylene thin film before (upper panel) and after (lower panel) water absorption while FIG. 5 shows XRD spectra of the surface of the polydiacetylene thin film before (upper) and after (lower) water absorption. FIG. 6 is a schematic view illustrating a structural change of the thin film upon water absorption. As can be seen in FIGS. 4 to 6, water absorption makes the thin film undergo a structural change, with the consequent color transition from a blue to a red phase.

Test Example 3: Thin Film Characterization 2

Figure 7:
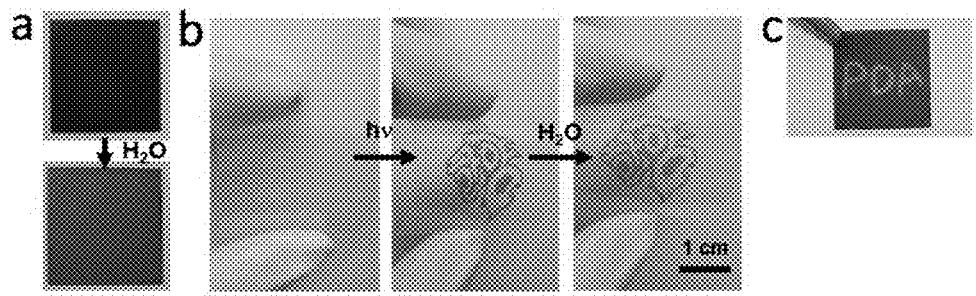
FIG. 7 shows photographic images of a hydrochromic thin film that undergoes chromatic transition upon exposure to water in accordance with an exemplary embodiment of the present invention.
Figure 8:
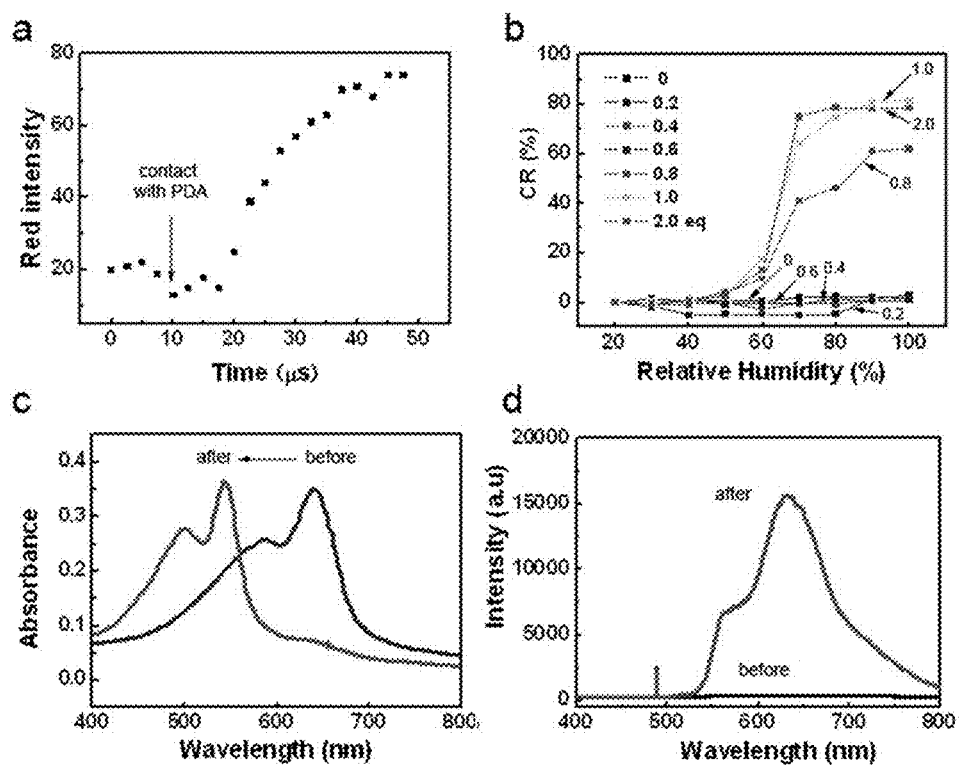
FIG. 8 shows graphs illustrating properties of hydrochromic thin films according to an exemplary embodiment of the present invention: color changes are plotted against time after a water drop is applied to the thin film (a); hydrochromic properties are depicted according to a molar ratio of PCDA and Cs ions (b); UV-Vis spectra before and after water absorption (c); and emission spectra before and after water absorption (d).

Properties of the thin films fabricated in Examples 2-1 and 3 were analyzed and the results are given in FIGS. 7 and 8. FIG. 7a shows the chromatic transition of the thin film fabricated in Example 2-1 from a blue to a red phase upon exposure to water while FIG. 7b shows the chromatic transition of the thin film according to Example 3, and the structural change of the thin film upon water absorption. FIG. 7c is an image of the thin film of Example 2-1 after chromatic transition occurred along letters written on the thin film with an aqueous ballpoint pen (letters appeared red). These thin films were observed to respond to water very quickly. It generally takes ones of seconds to ones of hours for typical hydrochromic materials to respond to water. In contrast, the hydrochromic polydiacetylene composite of the present invention responds to water as fast as 10 m/s. FIG. 8a is a graph in which red intensity is plotted against time after a water drop is applied to the thin film of Example 2-1, as measured by a high-speed camera. FIG. 8b shows hydrochromic properties of hydrochromic polydiacetylene composites prepared with various molar ratios of PCDA and Cs (in FIG. 8b, CR represents colorimetric response). For a desired colorimetric response to humidity, as can be seen in the graph, a molar ratio of PCDA:Cs is preferably set to be 1:0.8 or more, and more preferably 1:1. FIG. 8c shows UV-Vis spectra before and after water absorption, and FIG. 8d shows emission spectra before and after water absorption. In both graphs, water absorption caused chromatic transition.

Test Example 4: Thin Film Characterization 2

Figure 9:
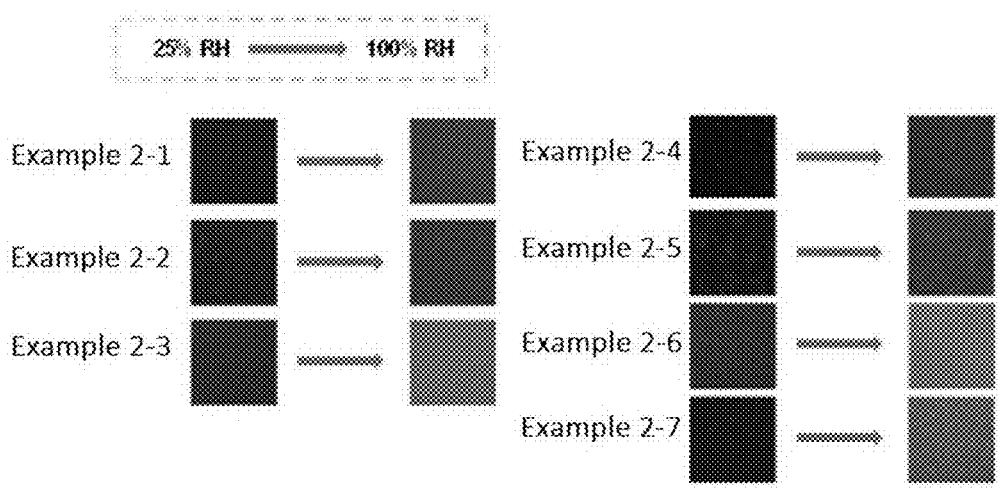
FIG. 9 shows photographic images of hydrochromic thin films that change in color with relative humidity in accordance with an exemplary embodiment of the present invention.
Figure 10:
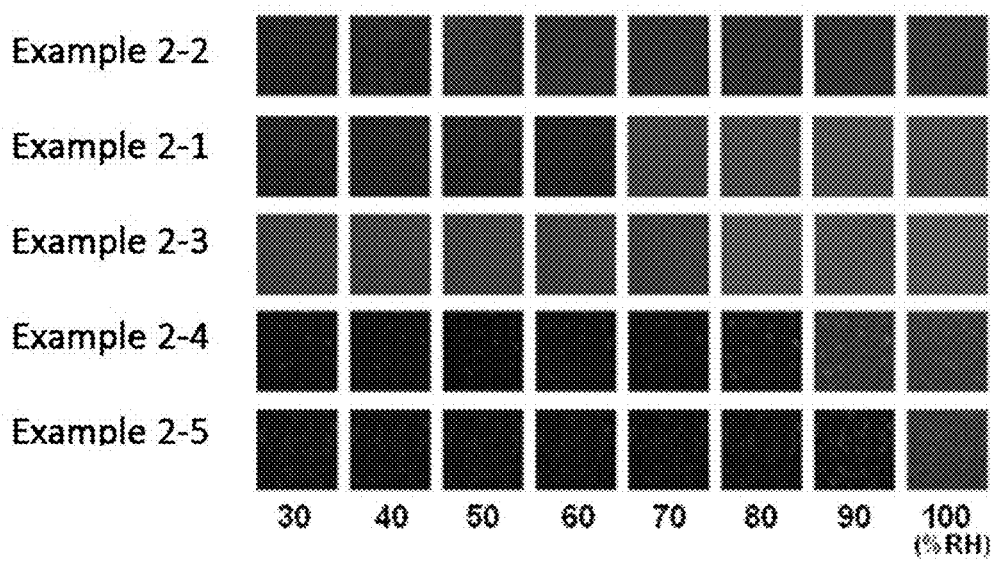
FIG. 10 shows humidity sensing ability of hydrochromic thin films in accordance with an exemplary embodiment of the present invention.
Figure 11:
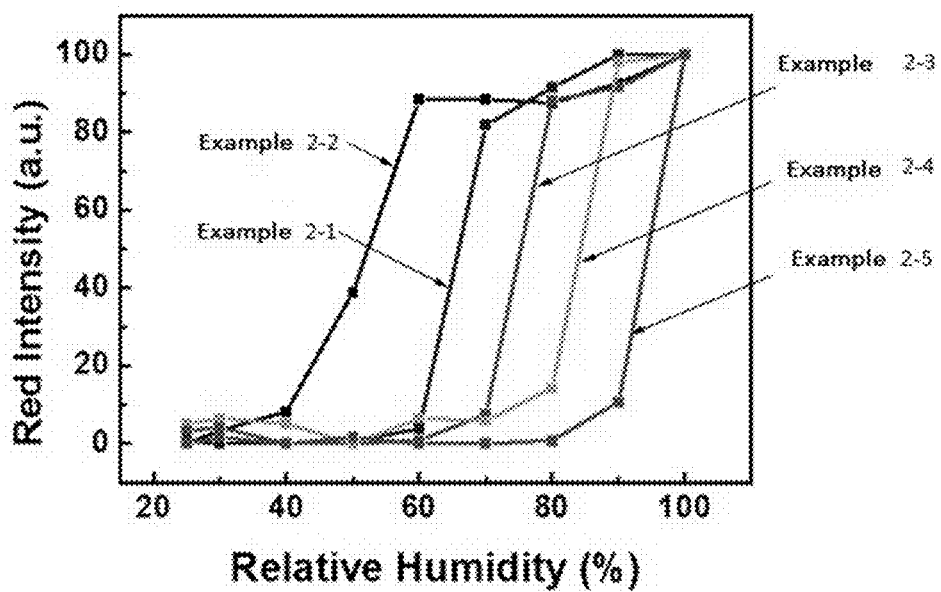
FIG. 11 is a graph showing color changes with humidity of the hydrochromic thin films according to an exemplary embodiment of the present invention.

The thin films fabricated in Examples 2-1 to 2-7 were analyzed for ability to sense water, and the results are shown in FIGS. 9 to 11. FIG. 9 shows color changes of the thin films with relative humidity (from 25% to 100%). All of the thin films appeared blue at 25% relative humidity, and turned red at 100% relative humidity. FIG. 10 shows humidity sensing test results of the thin films. Color transition started at about 50% relative humidity for Example 2-2, at about 60% relative humidity for Example 2-1, at about 70% relative humidity for Example 2-3, at about 80% relative humidity for Example 2-4, and at about 90% relative humidity for Example 2-5. FIG. 11 is a graph showing colors of the thin films according to humidity. As can be seen in FIGS. 10 and 11, the films can respond to 50%-100% relative humidity according to the structure of the diacetylene composite, implying that the structural control leads to adjusting the humidity sensitivity of the thin films. In addition, the data obtained above indicate that the thin films of the present invention can be used as humidity sensors highly responsive to a predetermined humidity value or higher.

Test Example 5: Manifestation of Sweat Pore Map by Hydrochromic Thin Film

Figure 12:
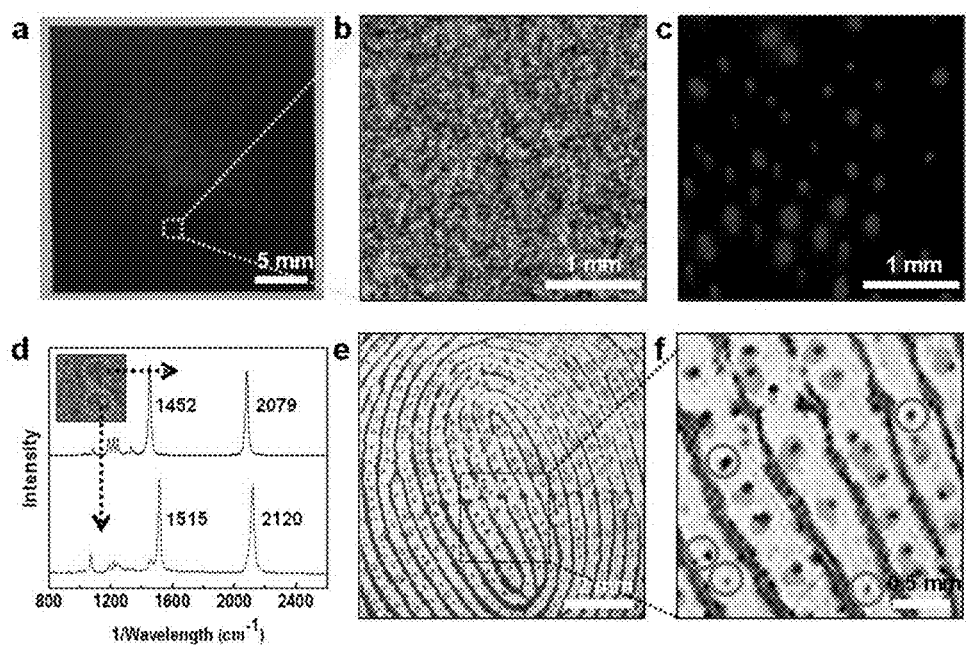
FIG. 12 illustrates a sweat pore mapping process using a hydrochromic thin film according to an exemplary embodiment of the present invention.

After sebaceous secretions and oils on a finger were cleaned off, the finger was lightly pressed against the hydrochromic thin film of Example 2-1 to obtain a sweat pore map as a trace amount of water from sweat pores made the thin film undergo chromatic transition selectively at the fingerprinted regions, and the map could be observed under a magnification glass or microscope, as shown in FIG. 12. Fluorescence microscopy of the sweat pores gave a fluorescent image manifesting the sweat pore distribution as a more distinct image, and thus is very suitable for comparative analysis. For examining a distribution of sweat pores, fingerprints were lightly impressed on two sheets of the blue thin film fabricated in Example 2-1, and observed under a microscope. The results are shown in FIG. 12. FIG. 12 shows images of the hydrochromic thin films that underwent chromatic transition due to a trace amount of water from sweat pores, taken by a camera (a), a microscope (b), and a fluorescence microscope (c). As can be seen in FIG. 12b, the thin films changed in color selectively in the impressed regions (appeared as red dots) due to water from sweat pores. In FIG. 12c, the red regions (dots) are more vividly observed. FIG. 12d shows Raman spectra of the microscopic images. Lower and upper portions of the circles correspond to the regions that have and have not undergone chromatic transition from a blue to a red phase in FIG. 12b, respectively. As can be seen in FIG. 12d, the diacetlyene composite was structurally transformed by water, which led to the chromatic transition. FIG. 12e is an image merged from an image obtained by a fingerprinting prism, showing a fingerprint and sweat glands, and the fluorescent image (c). FIG. 12f is a magnification of the image of FIG. 12e. As seen in FIG. 12f, the fluorescent results obtained from the film are consistent with the sweat pores identified by the prism. In FIG. 12f, the thin film was observed to not change in color at some regions corresponding to sweat pores (marked by circles), implying that some sweat pores do not secrete sweat. Therefore, the thin film of the present invention can be applied to medical data on whether sweat pores secrete sweat or not, as well as fingerprint recognition.

Test Example 6: Sweat Pore Mapping Using Hydrochromic Thin Film 1

Figure 13:
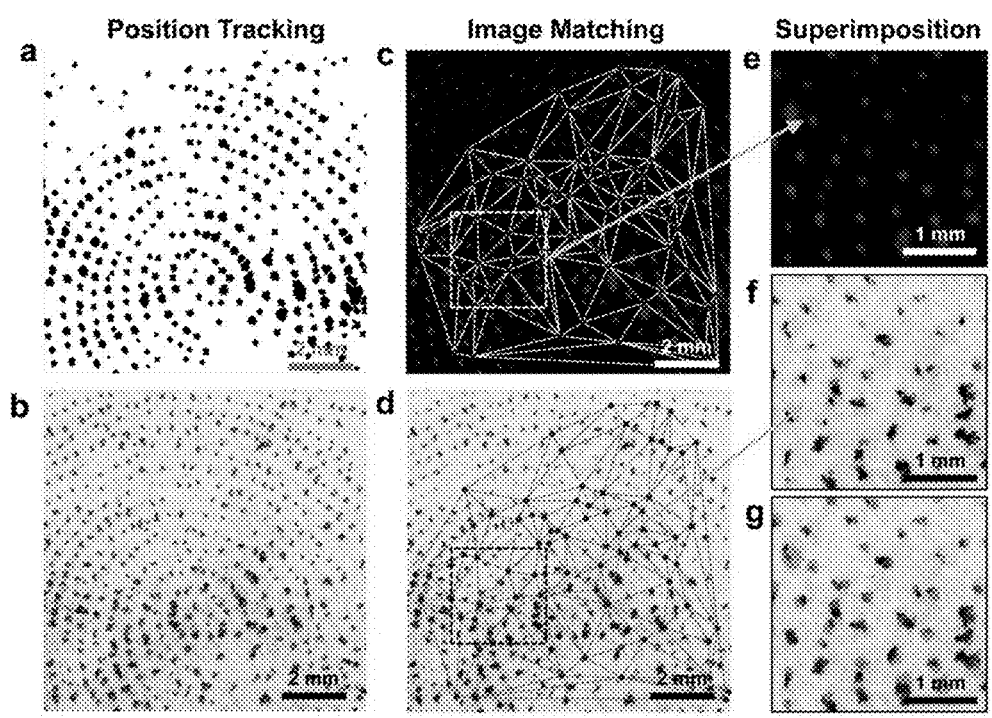
FIGS. 13 to 15 show analysis results of sweat pore maps manifested using hydrochromic thin films according to an exemplary embodiment of the present invention.

FIG. 13a is a threshold image of sweat pores alone manifested by position tracking on the film of Example 2-1 against which a finger was lightly pressed after the finger was washed to remove sebaceous secretions and oils, and dried. FIG. 13b is an image of sweat pores alone manifested by position tracking from a ninhydrin fingerprint image. FIGS. 13c (fluorescent image of FIG. 13a) and 13d are given to comparatively analyze whether the image of FIG. 13a is consistent with that of FIG. 13b. FIG. 13e is a magnified image of a specific part of FIG. 13c (red dots appeared only in the printed friction ridges due to sweat from sweat pores) while FIG. 13f is a magnified image of a specific part of FIG. 13d. FIG. 13g is an image merged from the fluorescent image of FIG. 13e and the image of FIG. 13f. As can be seen, the two images are consistent in sweat pore positions.

For additional verification, the same experiments were performed with fingerprints provided from five people, and the same results were obtained. In addition, a potential fingerprint of interest was successfully identified from a database of 10 fingerprints. Furthermore, the thin film of the present invention was successfully used in identifying the fingerprint providers from distorted fingerprints or even a part of a potential fingerprint. Hence, the present invention guarantees accurate fingerprinting analysis.

Test Example 7: Sweat Pore Mapping Using Hydrochromic Thin Film 2

Figure 14:
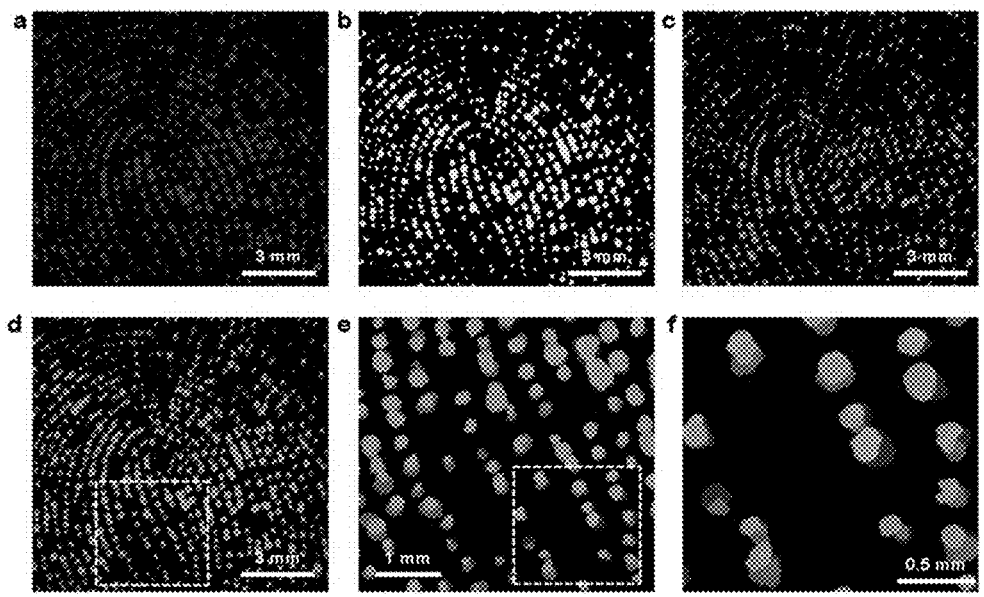

A finger was impressed on three sheets of the thin film of Example 2-1 at regular time intervals (after the finger was washed to cleanse off sebaceous secretions and oils therefrom, and dried). Sweat pore maps were manifested and analyzed by fluorescence microscopy. The results are shown in FIG. 14. FIGS. 14a to 14c are sweat pore maps of the fingerprints impressed at different times (all the films changed in color selective in the friction ridges impressed thereon while the sweat pores appear as red dots (a), yellow dots (b), and blue dots (c)). FIG. 14d is a merged image of FIGS. 14a to 14c. FIGS. 14e to 14f are magnified images of FIG. 14d. As apparent from FIG. 14, the three images are consistent with one another.

Test Example 8: Sweat Pore Mapping Using Hydrochromic Thin Film 3

Figure 15:
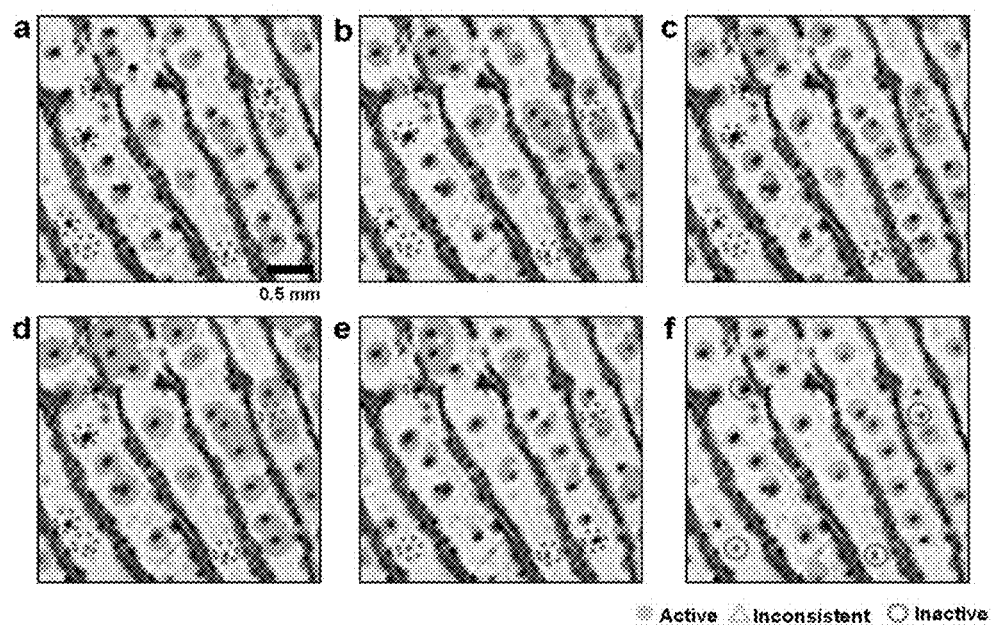

A finger was impressed on five sheets of the thin film of Example 2-1 at regular time intervals (after the finger was washed to cleanse off sebaceous secretions and oils therefrom, and dried). Sweat pore maps were manifested and analyzed by fluorescence microscopy. The results are shown in FIG. 15. FIGS. 15a to 15e are sweat pore maps of the fingerprints impressed at different times (in FIGS. 15a to 15e, active sweat pores are marked by red dotted shade circles while inactive sweat pores are marked by blue dotted circles). FIG. 15f is an image analyzing the results of FIGS. 15a to 15e. In FIG. 15f, consistently active sweat pores are marked by red shaded circles, partially active sweat pores by yellow triangles, and consistently inactive sweat pores by blue circles. As a rule, innumerable sweat pores are on the human body, but become inactive with age. That is, many sweat pores are present in the body, but not all release sweat. The degree of inactivation is different from one sweat pore to another. According to the present invention, therefore, it is possible to examine whether sweat pores are active or inactive, which may be used as medical data. Further, an additional experiment showed that sweat pore maps can be obtained from any region of the body where sweat pores are present, like a sole of the foot, a face, an arm, etc.

Test Example 9: Sweat Pore Mapping Using Hydrochromic Thin Film 4

Figure 16:
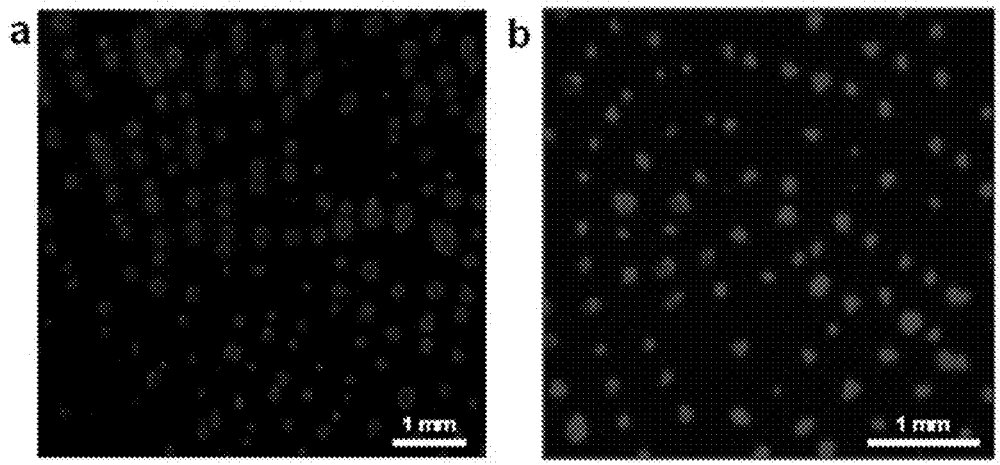
FIG. 16 shows fluorescence microimages of sweat pore maps manifested using hydrochromic thin films according to an exemplary embodiment of the present invention.

Images were respectively obtained by lightly pressing a finger against the films of Examples 2-3 and 2-5 after the finger was washed to remove sebaceous secretions and oils therefrom, and dried. The images were analyzed by fluorescence microscopy. The results are depicted in FIG. 16. As can be seen in FIG. 16, the thin films underwent chromatic transition selectively at the friction ridges impressed, and allowed for the construction of detailed sweat maps (color changed portions represented as dots). The hydrochromic thin films of Examples 2-3 (PCDA-Rb) and 2-5 (TCDA-K) were also observed to manifest sweat pore maps.

Figure 17:
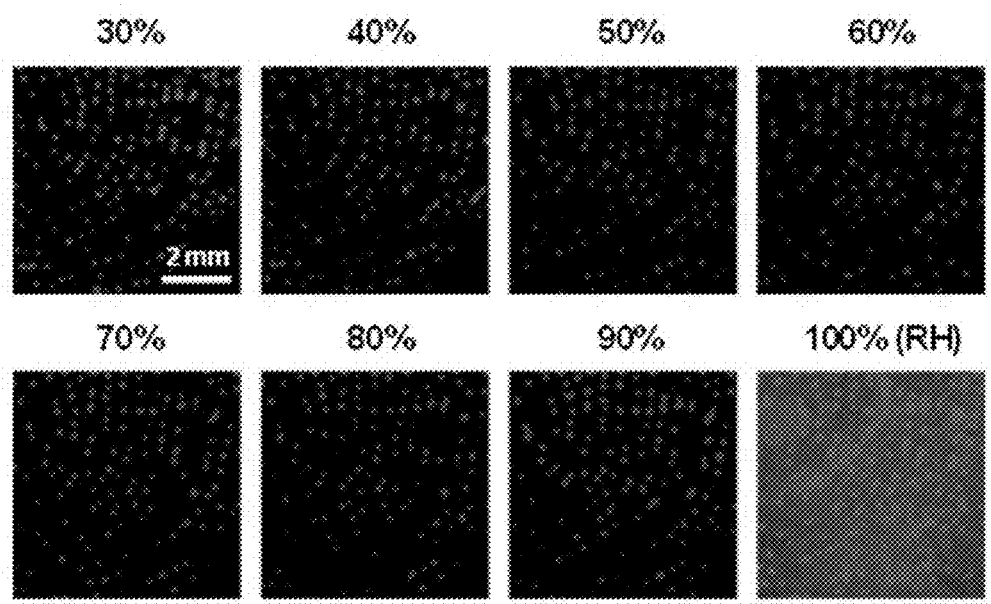
FIG. 17 shows fluorescence microimages of sweat pore maps manifested at different relative humidities using hydrochromic thin films according to an exemplary embodiment of the present invention.

Moreover, the hydrochromic thin film of Example 2-5 (TCDA-K) was analyzed for sweat pore mapping according to humidity by fluorescence microscopy. The results are given in FIG. 17. As can be seen in FIG. 17, the hydrochromic thin film allowed for sweat pore mapping even at a relative humidity of 90% or higher, demonstrating its stability to humidity.

Test Example 10

Figure 18:
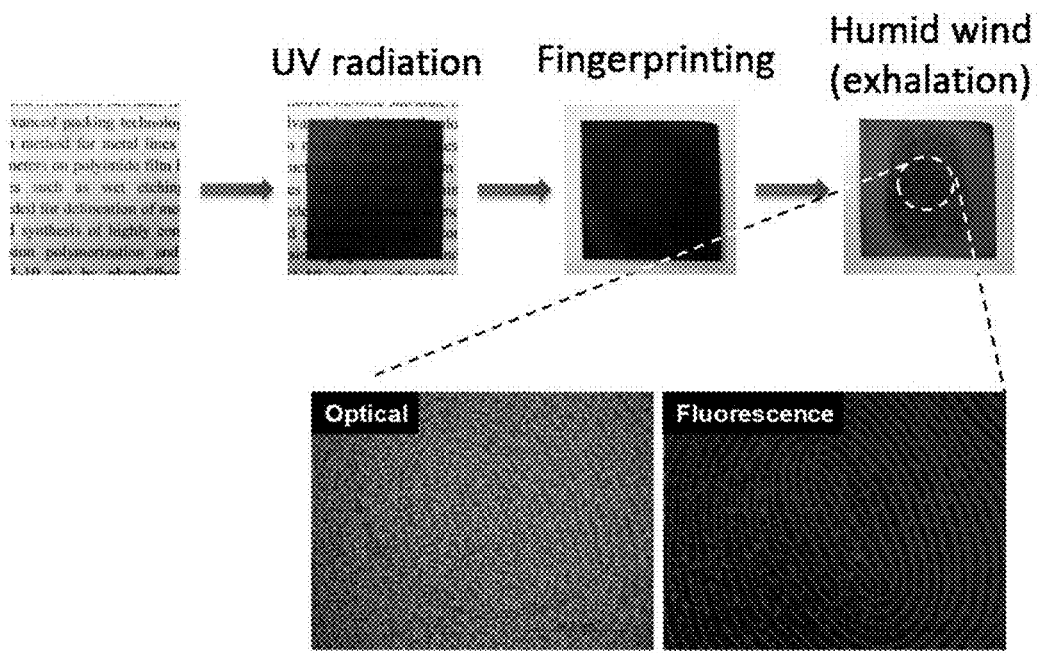
FIG. 18 illustrates the manifestation of a fingerprint on a thin film according to an exemplary embodiment of the present invention.

Fingerprint Manifestation and Analysis as shown in FIG. 18, a finger was strongly pressed against a blue thin film that was fabricated by applying a composition of the present invention onto a PET film substrate and photopolymerizing the composition. In this regard, the fingerprint impressed on the blue thin film was not visualized with the naked eye. When the blue film was exhaled upon, the impressed fingerprint remained blue and the other portions turned red as sebaceous secretions and oils distributed over the friction ridges acted as a protective layer against water penetration. Thus the fingerprint was manifested.

Figure 19:
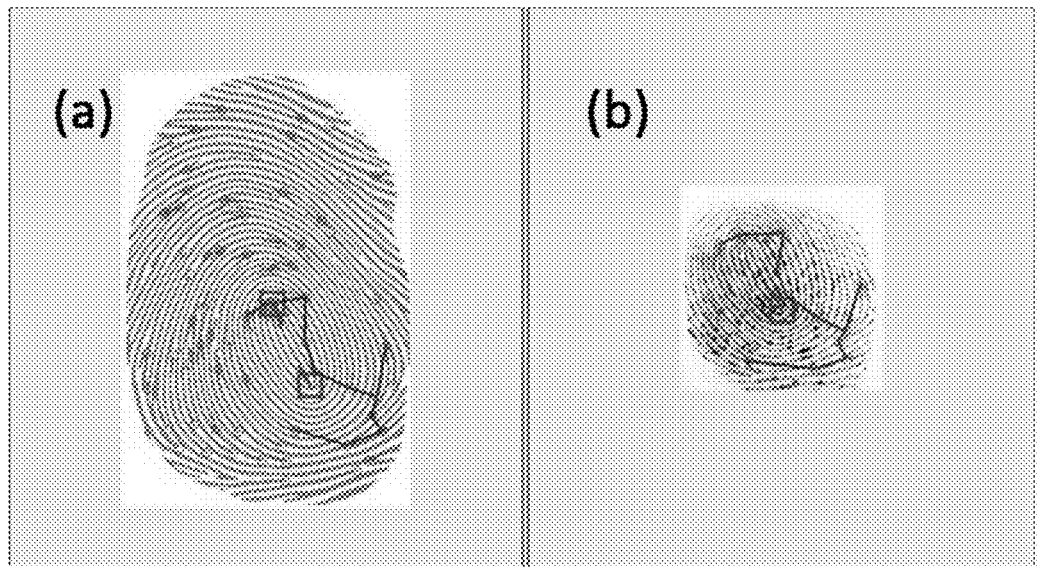
FIG. 19 shows analysis results after data of a potential fingerprint obtained using a fingerprint reader and a fingerprint recognition program are compared.

The manifested fingerprint was compared with the fingerprint data of the fingerprint provider. The manifested fingerprint of the provider was analyzed for characteristics (core, delta, ridge end, bifurcation, etc.) using commercially available software, and the result is given in FIG. 19*a*. And the result from the fingerprint data of the fingerprint provider obtained using a commercially available fingerprint reader is given in FIG. 19*b*. As can be seen in FIG. 19, the results are correctly consistent with each other.

The present invention can visualize even a partial sweat pore distribution as well as a fingerprint image, whether vivid or faint, into an amplified fluorescent image, thereby achieving fingerprint recognition at near 100% accuracy. Because people have their own characteristic sweat pore distributions, even a sweat pore map containing a very small portion of sweat pore distribution can be used to identify a person of interest. In other words, results obtained by analyzing sweat pore features of a fingerprint provider using a fingerprint reader, and results obtained by manifesting fluorescent sweat pore patterns of a fingerprint using fingerprint recognition software can be combined with each other to identify the acquired fingerprints at near 100% accuracy. Thus, the present invention can be used in edge-cutting forensic science and for developing new dermatoglyphics technology. In addition, the present invention is very advantageous in that even a part of sweat pore distribution can be useful for fingerprint recognition.

All patents, applications, standards, and articles noted herein are hereby incorporated by reference in their entirety.

What is claimed is:

1. A method of sensing moisture, comprising: providing a polydiacetylene composite composition including a polydiacetylene polymerized from diacetylene monomers that are complexed with an alkali metal ionic compound to give a diacetylene composite, and
   detecting color or fluorescent transition of the polydiacetylene composite composition after exposing the polydiacetylene composite composition to the moisture,
   wherein each of the diacetylene monomers is a compound represented by the following Chemical Formula (2), or an mBzA compound in which a benzamide group is incorporated into a diacetylene molecule,

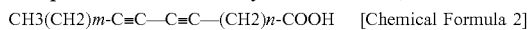   [Chemical Formula 2]

wherein m+n is an integer of 2 to 50.

2. The method of claim 1, wherein the alkali metal is any one selected from the group consisting of cesium, rubidium, and potassium.

3. The method of claim 1, wherein the diacetylene monomers include at least one selected from the group consisting of PCDA (10,12-pentacosadiynoic acid), TCDA (10,12-tricosadiynoic acid), HCDA (8, 10-heneicosadiynoic acid), PCDAmBzA, TCDA-mBzA and HCDA-mBzA.

4. The method of claim 1, wherein the diacetylene composite includes at least one selected from the compounds represented by the following Chemical Formula (3), Chemical Formula (4), and Chemical Formula {5}:

   [Chemical Formula 3]

wherein m+n is an integer of 2 to 50,

   [Chemical Formula 4]

wherein m+n is an integer of 2 to 50,

   [Chemical Formula 5]

wherein m+n is an integer of 2 to 50.

5. The method of claim 1, wherein the moisture is included in the atmosphere, and the method is for sensing humidity.

6. The method of claim 1, wherein the moisture is sweat secreted from sweat pores, and the method is for sensing sweat pores.

7. The method of claim 6, wherein the polydiacetylene composite composition is provided as a layer on a thin film substrate, and the exposing the polydiacetylene composite composition to the sweat secreted from sweat pores is contacting a skin having the sweat pores against the layer.

8. The method of claim 7, wherein the skin having sweat pores is included in a finger and has a fingerprint.

9. The method of claim 1, wherein the polydiacetylene composite composition is provided as a layer on a thin film substrate.

* * * * *